(12) United States Patent
Dikeman

(10) Patent No.: US 7,241,285 B1
(45) Date of Patent: Jul. 10, 2007

(54) MEDICAL SITE CONNECTION

(75) Inventor: W. Cary Dikeman, Leawood, KS (US)

(73) Assignee: Medical Ventures, Inc., Leawood, KS (US)

(*) Notice: Subject to any disclaimer, the term of this patent is extended or adjusted under 35 U.S.C. 154(b) by 35 days.

(21) Appl. No.: 11/005,151

(22) Filed: Dec. 6, 2004

(51) Int. Cl.
*A61M 25/16* (2006.01)

(52) U.S. Cl. .................................... 604/533

(58) Field of Classification Search ........... 251/149.1; 604/537, 533, 249, 905, 256, 167.01, 167.03, 604/265
See application file for complete search history.

(56) References Cited

U.S. PATENT DOCUMENTS

| | | | |
|---|---|---|---|
| 4,765,588 A | 8/1988 | Atkinson | |
| 4,991,629 A | 2/1991 | Ernesto et al. | |
| 5,088,984 A | 2/1992 | Fields | |
| 5,135,489 A | 8/1992 | Jepson et al. | |
| 5,251,873 A * | 10/1993 | Atkinson et al. | 251/149.1 |
| 5,437,650 A | 8/1995 | Larkin et al. | |
| 5,501,426 A | 3/1996 | Atkinson et al. | |
| 5,533,708 A | 7/1996 | Atkinson et al. | |
| 5,536,262 A | 7/1996 | Velasquez | |
| 5,603,706 A | 2/1997 | Wyatt et al. | |
| 6,096,011 A * | 8/2000 | Trombley, III et al. | 604/256 |
| 6,146,362 A | 11/2000 | Turnbull et al. | |
| 6,213,996 B1 * | 4/2001 | Jepson et al. | 604/533 |
| 6,358,236 B1 | 3/2002 | DeFoggi et al. | |
| 6,440,107 B1 | 8/2002 | Trombley, III et al. | |
| 6,605,076 B1 | 8/2003 | Jepson et al. | |
| 6,626,418 B2 | 9/2003 | Kiehne | |
| 6,652,509 B1 | 11/2003 | Helgren et al. | |
| 6,706,031 B2 | 3/2004 | Manera | |
| 2002/0143297 A1 | 10/2002 | Frankavilla et al. | |
| 2002/0188274 A1 | 12/2002 | Azzolini | |
| 2004/0068238 A1 * | 4/2004 | Utterberg et al. | 604/256 |
| 2004/0068239 A1 | 4/2004 | Utterberg et al. | |

* cited by examiner

*Primary Examiner*—Nicholas D. Lucchesi
*Assistant Examiner*—Christopher D. Koharski
(74) *Attorney, Agent, or Firm*—Stevens & Showalter LLP

(57) ABSTRACT

A connector for connecting a fluid passage device, such as may be provided by a luer taper, and an injection site having a thin diaphragm, and method of forming a medical coupling site connection between the fluid passage device and the injection site. The connector includes a reduced diameter cannula for engaging the thin diaphragm sufficiently to open the thin diaphragm to establish an open fluid passage. The connector is further disclosed as including an enlarged annular land portion surrounding the cannula for forming an interference fit within a retention portion of the injection site.

6 Claims, 3 Drawing Sheets

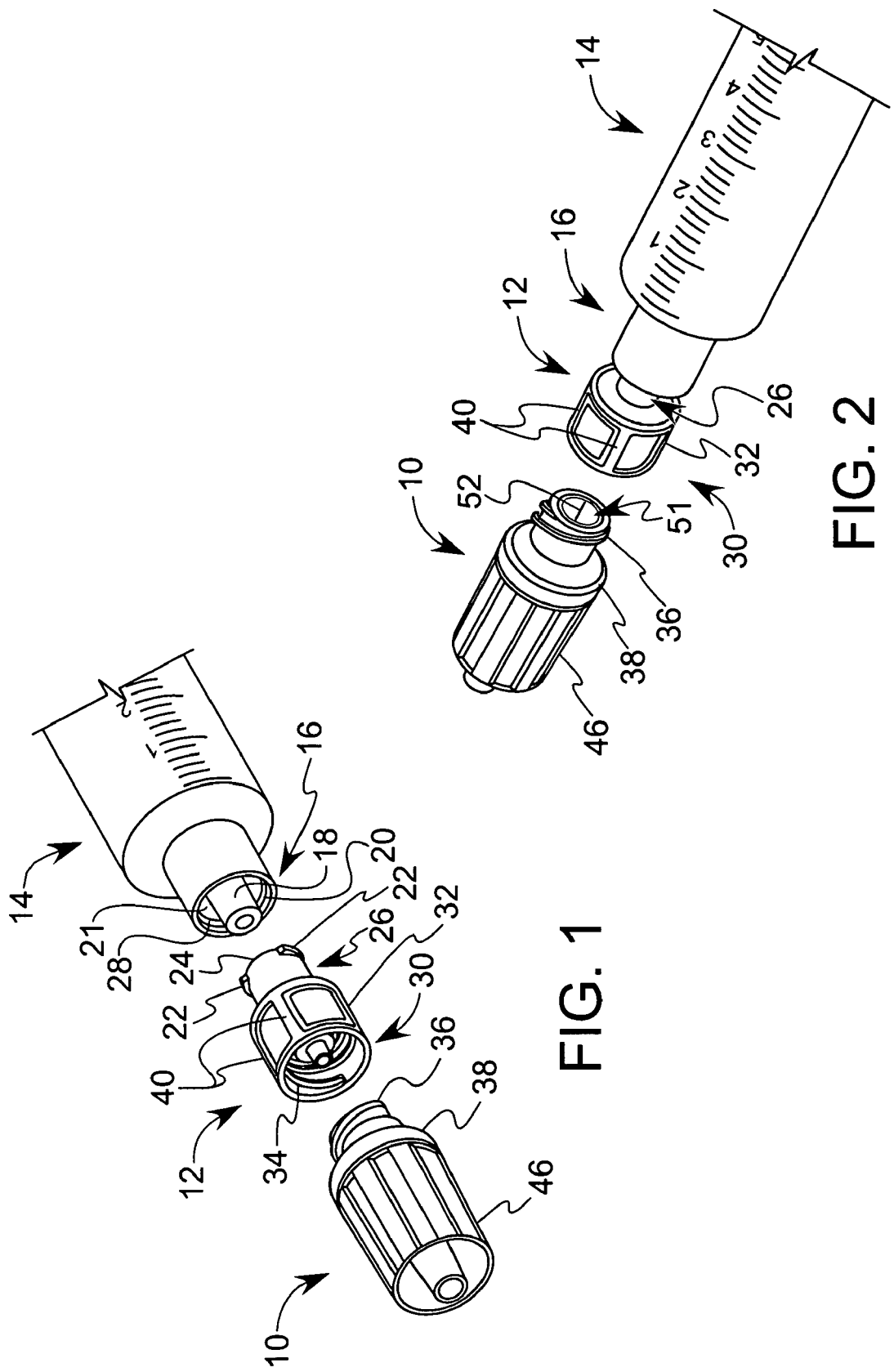

MEDICAL SITE CONNECTION

BACKGROUND OF THE INVENTION

The present invention relates to a medical site connection for use in medical applications and more particularly, to a connector for forming a connection to a needleless injection site, which may include an elastomeric valve body having a thin diaphragm with a diametrically extending slit. A method of providing such a connection is also provided.

There is a recognized need for eliminating needles for use with injection sites in order to avoid the disadvantages therewith including the possibility of medical personnel receiving a puncture wound and the progressive deterioration of the diaphragm resulting from repetitive puncturing of the diaphragm.

As discussed in the background of U.S. Pat. No. 5,533,708, there have been several proposed solutions to fulfill this need. One proposed solution for eliminating needles at coupling sites includes providing a valve member having a slit for receiving a blunt cannula therethrough wherein the slit is biased to a closed position such that a fluid-tight seal is formed at the valve member when the cannula is removed.

Both the American National Standards Institute, Inc. (ANSI) and the International Organization for Standardization (ISO) have recognized standard dimensions for both male and female luer taper fittings. Thus, the fittings formed on the ends of syringes, as well as fittings for the majority of fluid connections used in medical applications throughout the world, conform to the ANSI and ISO standards.

Additional considerations involved with needleless injection sites include certain physical design limitations associated with a valve element which will both receive a luer taper as well as reliably reseal after the luer taper is removed. Several prior art valves for receiving a luer taper provide a thick disk or septum, such as is disclosed in U.S. Pat. No. 5,135,489, wherein the disk or septum is formed with a sufficient amount of resilient material around the slit to close the slit when a cannula is not present. Space must be provided in order to accommodate the distortion of material around the slit as the cannula is inserted and this space must either be provided within the fluid passage area for receiving the cannula or within the housing supporting the disk or septum, such as may be provided by an annular space directly adjacent to the outer periphery of the disk or septum.

Alternatively, the slit may be formed in a relatively thin diaphragm, such as is disclosed in U.S. Pat. No. 4,765,588 to Atkinson, wherein sufficient space for receiving the distorted portions of the diaphragm around the slit is provided within a space defined by the tubular body portion for receiving the luer taper. Additional improvements to providing a medical coupling site having a relatively thin diaphragm are also found in U.S. Pat. No. 5,533,708 to Atkinson.

As there are many design constraints associated with connecting medical devices, such as syringe luer locks, and needleless injection sites, a connector adapting the medical device to the injection site may be desirable to provide an improved coupling site connection.

Accordingly, there is a need for an improved medical fluid path coupling site connection for attaching a needleless injection site to a medical device, such as on a standard syringe.

SUMMARY OF THE INVENTION

In accordance with one aspect, the present invention provides medical site connector for connecting a syringe and a needleless injection site having a thin diaphragm, the connector comprising a cannula for engaging the thin diaphragm sufficiently to open the thin diaphragm to establish an open fluid passage wherein the cannula has a reduced diameter, and an enlarged annular land portion surrounding the cannula for forming an interference fit within a retention portion of the needleless injection site.

In accordance with a further aspect, the present invention provides a medical coupling site comprising a needleless injection site including a housing and a valve element comprising a diaphragm retained within the housing, wherein the diaphragm includes a slit defined by opposing slit edges, and a connector having a cannula for engaging an exterior surface of the diaphragm with a pressure sufficient to open the slit to establish an open fluid passage.

In accordance with another aspect, the invention provides a method of providing a medical coupling site connection between a fluid passage device and an injection site having a diaphragm retained within a housing, the method including the steps of providing a connector having a cannula defining a fluid passage through the connector and a collar surrounding the cannula, providing a first end of the connector attached to the fluid passage device, attaching a second end of the connector to the injection site by moving the connector onto the injection site to move the cannula toward the diaphragm, and limiting movement of the cannula toward the diaphragm to define a maximum insertion extent of the cannula where the cannula presses on an exterior surface of the diaphragm to stretch the diaphragm and open the diaphragm for fluid passage through the injection site.

Other features and advantages of the invention will be apparent from the following description, the accompanying drawings and the appended claims.

BRIEF DESCRIPTION OF THE DRAWINGS

FIG. 1 is a perspective view of a medical coupling site assembly, generally including a needleless injection site, an adapter constructed in accordance with the present invention, and an end portion of a standard syringe, prior to attachment;

FIG. 2 is a perspective view of a medical coupling site assembly, generally including a needleless injection site and an adapter constructed in accordance with the present invention attached to an end portion of a standard syringe;

DETAILED DESCRIPTION OF THE INVENTION

Figures 3, 4:
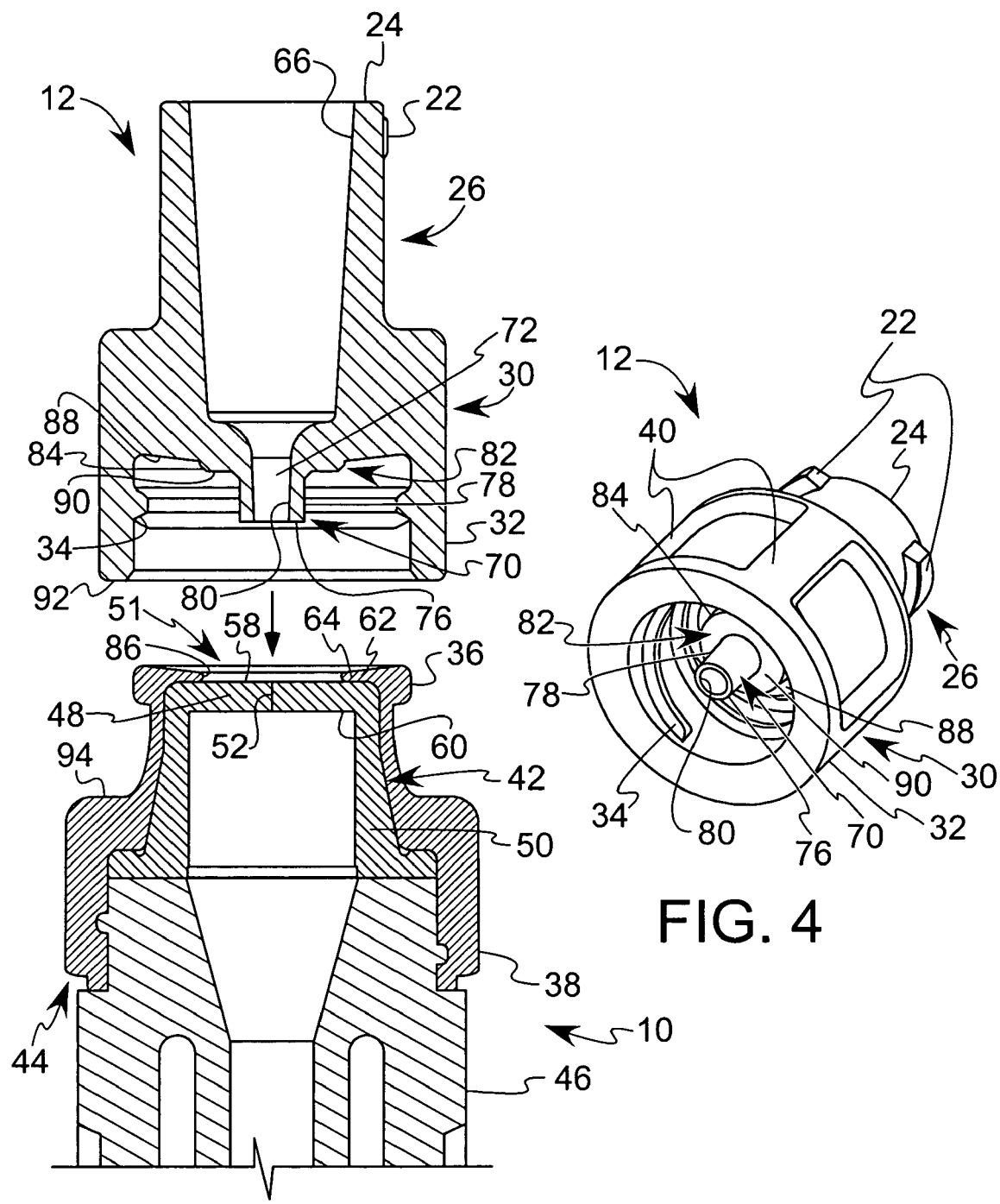
FIG. 3 is a cross-sectional view of an adapter constructed in accordance with the present invention and a needleless injection site, prior to attachment.
FIG. 4 is a perspective view of an adapter constructed in accordance with the present invention.

As shown in the drawings and described herein with reference to specific embodiments of the present invention, this disclosure is to be considered as an exemplification of the principles of the invention and is not intended to limit the invention to the specific embodiments illustrated. In referring to the attached drawings, it should be noted that corresponding elements in the several Figures include common reference numbers.

Referring to FIG. 1, a perspective view of a medical coupling site assembly is shown, generally including a needleless injection site 10, a medical site connector illustrated as an adapter 12 constructed in accordance with the present invention, and a fluid passage device illustrated as an end portion of a standard syringe 14 that preferably includes a standard luer lock 16 comprising a luer taper 18 surrounded by a threaded locking collar 20 to define an annular space 21 therebetween. The adapter 12 is configured to be attached to the luer lock 16 and forms an interface between the syringe 14 and the needleless injection site 10, as described further below.

Referring to FIGS. 1 and 2, the adapter 12 preferably includes a pair of lug portions 22 located near a first end 24 of a first portion 26 of the adapter 12 for engaging the luer lock 16, where the first portion 26 of the adapter 12 is received in the annular space 21 of the luer lock 16 to engage the lug portions 22 with the threads 28 of the threaded locking collar 20 whereby the adapter 12 will be held in positive mechanical locking engagement with the luer lock 16. The lug portions 22 are generally configured to engage the double helix threads 28 formed on the interior of a threaded locking collar 20 for a standard male luer lock 16. Thus the lug portions 22 may be formed extending at a slight angle relative to a plane extending perpendicular to a longitudinal axis extending through the adapter 12. In addition, it should be noted that the lug portions 22 may be configured as threads extending around the circumference of the first portion 26 of the adapter 12. It should be noted that the present adapter 12 is specifically designed for cooperation between a standard male luer lock having standardized dimensions, such as specified by ANSI and ISO standards, and a needleless injection site which may also have standardized dimensions and valve characteristics, as described further below.

A second portion 30 of the adapter 12 is illustrated as including a collar 32 defining a diameter larger than the diameter of the first portion 26, and having interior threads 34 for engaging an outer surface 36 of a cap portion 38 of the needless injection site 10 in threaded engagement. Additionally, the second portion 30 of the adapter 12 may include external ribs 40 for facilitating tactile engagement of the adapter 12 when attaching and removing the adapter 12 from the associated components. The adapter 12 may be formed of any plastic or equivalent material typically used in such medical applications.

Referring to FIG. 3, the adapter 12 is configured to form a fluid connection with a needleless injection site 10 comprising an elastomeric valve element 42 located within a housing 44 defined by a base 46 and a cap portion 38. The valve element 42 preferably includes a thin, flexible diaphragm 48 formed integrally with a tubular body portion 50. The tubular body portion 50 supports the diaphragm 48 at an exposed insertion end 51 of the injection site 10, and the diaphragm 48 includes a diametrically extending slit 52 (see also FIG. 2) defined by opposing slit edges 54, 56 (shown in FIG. 6). The slit 52 may be opened by a force or pressure applied to an exterior surface 58 of the diaphragm 48, and the tubular body portion 50 supports the diaphragm 48 around the peripheral edge 60 of the diaphragm 48 to facilitate biasing the diaphragm 48 toward its closed position in the absence of an opening force. The cap portion 38 includes an inwardly extending flange 62 defining a retention portion 64 surrounding the exterior surface 58 of the diaphragm 48 at the insertion end 51. It should be noted that the base 46 and cap portion 38 are formed of a medical grade plastic or equivalent material for forming a relatively rigid housing structure for the valve element 42. The valve element 42 used with the present invention may have a configuration similar to that disclosed in U.S. Pat. No. 5,533,708 or U.S. Pat. No. 5,501,426 both issued to Atkinson which are hereby incorporated by reference, or any other thin diaphragm.

Figure 6:
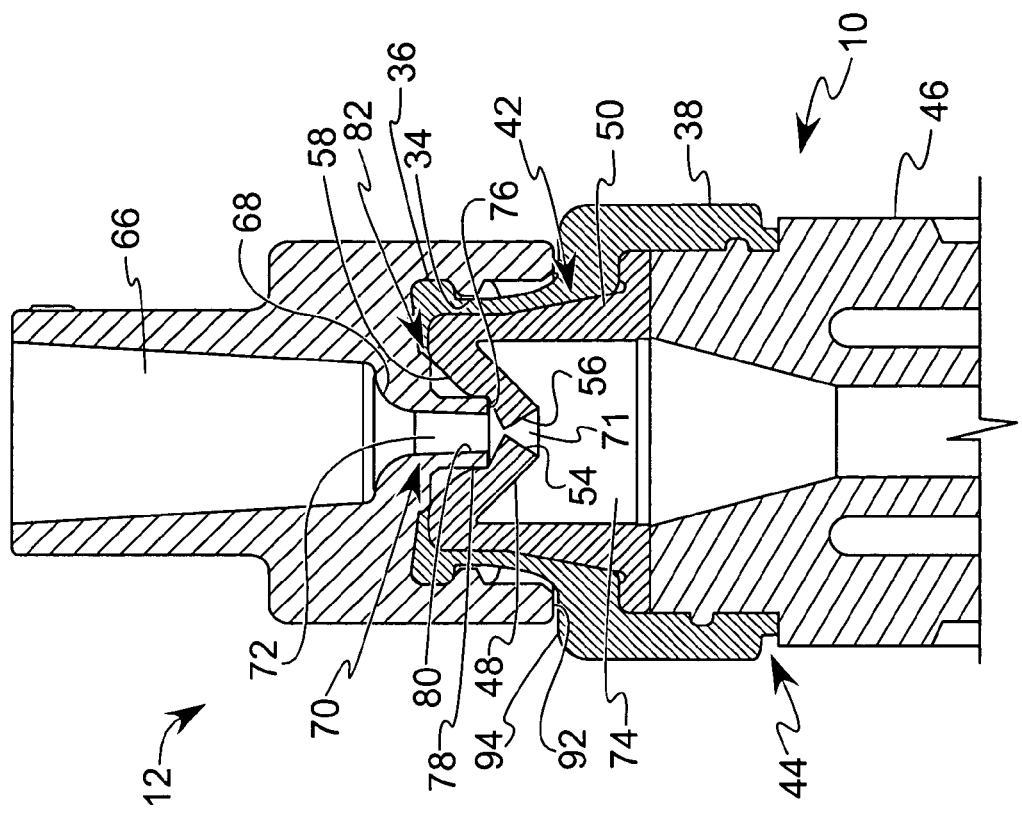
FIG. 6 is a cross-sectional view of an adapter constructed in accordance with the present invention and a needleless injection site, after attachment.
Figure 5:
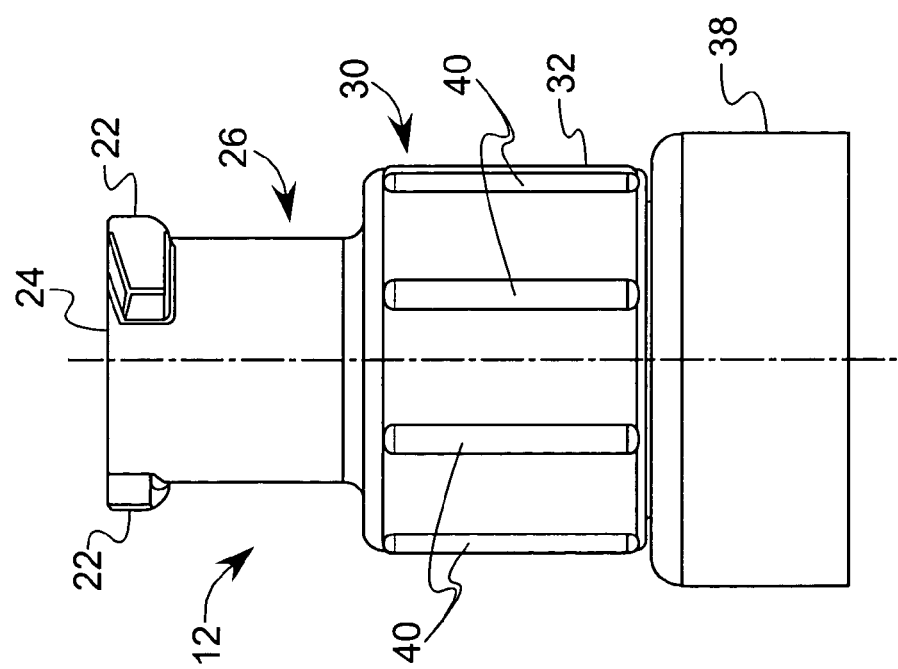
FIG. 5 is a side view of an adapter constructed in accordance with the present invention and a cap of a needleless injection site, after attachment.

Referring further to FIGS. 4–6, the adapter 12 is illustrated connected to the cap portion 38 of the needleless injection site 10. The adapter 12 includes a fluid passage area 66 into which the luer taper 18 of a standard syringe 14 fits when the first portion 26 of the adapter 12 is positioned in the annular space 21 of the luer lock 16. Fluid passage area 66 includes a taper 68 providing a surface against which the luer taper 18 of a standard syringe 14 fits with an interference fit to prevent fluid from passing outside of the adapter 12. Fluid passage area 66 continues tapering to a cannula 70 having a diameter smaller than, or reduced compared to, the luer taper 18 of the standard syringe 14. The cannula 70 also has a length such that when the adapter 12 is fully engaged with the cap portion 38 of the needleless injection site 10, the cannula 70 extends into the diaphragm 48 only far enough to open the slit 52, providing or establishing an open fluid passage 71, as shown in FIG. 6, and no more than necessary to open the valve 42. In other words, the cannula 70 extends only as far as required for the cannula passage 72 to be placed in fluid contact with the interior 74 of the needleless injection site 10. The cannula 70 may have a blunt end 76 for engaging the diaphragm 48 and, by way of example, may open the diaphragm 48 an extent to define a flow area through the slit 52 equal to or greater than the flow area at the end of the cannula 70. In such an open position, the opposing edges 54, 56 defining the diaphragm slit 52 are spaced, at a maximum extent of separation, a distance which is less than the diameter of the outer surface 78 of the cannula 70 for the adapter 12, and which may be substantially equal to or less than the diameter of the inner surface 80 of the cannula 70 defining the flow passage through the cannula 70.

Referring to FIGS. 3, 4 and 6, the cannula 70 of the adapter 12 is surrounded by an annular land portion 82 having an outer surface 84 having a diameter that is greater than the diameter of the outer surface 78 of the cannula 70, and that is slightly greater than a diameter of an inner surface 86 defined by the retention portion 64. The surrounding enlarged annular land portion 82 extends axially from a back interior surface 88 of the adapter 12 and engages within the retention portion 64 defined by the cap portion 38 in a frictional interference fit. The surrounding enlarged annular land portion 82 also includes a forward surface 90 which engages with or close to the exterior surface 58 of the diaphragm 48, preventing leakage at the diaphragm 48. The frictional interference fit and/or the positioning of the forward surface 90 at the exterior surface 58 of the diaphragm 48 provides a secure seal and closer fit at the exposed exterior surface 58 of the diaphragm 48, preventing leakage of fluids and limiting fluid collection at the exterior surface 58 of the diaphragm 48. Additionally the adapter 12 includes a shoulder 92 at a forward end of the adapter collar 32 which may be dimensioned in an axial direction to engage with a cooperating surface 94 of the housing 44 for the needleless injection site 10 to limit engagement of the cannula 70 of the adapter 12 and the diaphragm 48. Alternatively and/or additionally, rotational movement of the adapter 12 relative to the housing 44 to engage the adapter 12 on the injection site 10 may be limited to control or limit axial movement of the cannula 70 toward the diaphragm 48 defining a maximum insertion extent of the cannula 70. Thus, the cannula 70 does not completely penetrate the slit 52 as generally occurs in known systems providing engagement of a luer taper 18 with an injection site 10. The smaller diameter of the cannula 70 and/or the controlled insertion extent of the cannula 70 toward the diaphragm 48 can reduce flexing of the diaphragm 48. Additionally, the smaller diameter of the cannula 70 and/or the controlled insertion extent of the cannula 70 toward the diaphragm 48 can eliminate or minimize leakage of fluids at the connection formed at the diaphragm slit 52 and/or eliminate or minimize reflux of fluids to the injection site 10 or to the adapter 12 during removal of the fluid connection from the injection site 10. Also, it may be noted that in the illustrated embodiment of the adapter 12, the cannula 70 is provided with an axial extent or length that does not extend beyond the forward end or shoulder 92 of the adapter collar 32, such that the adapter cannula 70 is fully surrounded by the collar 32 and substantially protected from contact during handling of the adapter 12.

In use, the adapter 12 of the present invention is used for providing a medical coupling site including, for example, a standard luer lock 16, such as part of a standard syringe 14 or other medical device, and a needleless injection site 10 having a thin diaphragm 48 as described above. A first end of the adapter 12 is attached to the luer lock 16 in a positive mechanical locking engagement and a second end of the adapter 12 is attached to the needleless injection site 10 having a thin diaphragm 48 so that the reduced diameter cannula 70 of the adapter 12 extends toward the diaphragm 48 an extent that is only sufficient or far enough to provide or establish an open fluid passage 71, and the enlarged annular land portion 82 of the adapter 12 engages within a retention portion 64 of the needleless injection site 10 in a frictional interference fit.

Although the preceding description includes a standard syringe, it should be understood that a standard luer lock or other known standard or non-standard medical devices defining a fluid passage may be used in cooperation with the connector of the present invention. Further, although the present embodiment of the invention has been described with reference to mechanical locking connections, such as threaded connections, between cooperating parts, it should be understood that the present invention is not limited by such connections. For example, the present invention may be practiced with other connections such as, without limitation, friction and interference connections.

In addition, the connector of the present invention may be incorporated integrally with an end of a syringe, such as in place of a standard luer lock structure, or may be formed at the end of any other device forming a passage for fluid.

Further, it should be understood that movement of the cannula of the connector toward the valve element may be limited by other structure than the structure explicitly described herein. For example, without limitation, the annular portion or an interior surface of the connector may additionally comprise structure for engaging against a surface of the injection site housing, such as a portion of the cap portion extending around the retention portion, whereby axial movement of the cannula is limited. Alternatively, without limitation, the annular portion may include at least a portion dimensioned to limit movement of the annular portion into engagement with the retention portion of the cap portion of the injection site to define the extent of axial movement for the cannula.

From the preceding description, it is understood the numerous variations and modifications may be effected without departing from the spirit and scope of the novel concept of the invention. It is to be understood that no limitation with respect to the specific apparatus illustrated herein is intended or should be inferred. It is, of course, intended to cover by the appended claims all such modifications as fall within the scope of the claims.

What we claim is:

1. A medical site connector for connecting a fluid passage and a needleless injection site, the needleless injection site comprising a housing and a valve element contained within the housing, the valve element having a thin diaphragm and the housing having an inwardly extending flange defining an inner surface surrounding an exposed surface of the thin diaphragm, the connector comprising:
    a cannula for engaging the exposed surface of the thin diaphragm sufficiently to open the thin diaphragm to establish an open fluid passage wherein the cannula has a reduced diameter smaller than the diameter of the inner surface of the flange;
    a collar surrounding the cannula for engaging the housing of the injection site; and
    an enlarged annular land portion extending axially from a back interior surface of the connector and surrounding the cannula, the annular land portion defining an outer surface for engaging within the inner surface of the flange for forming an interference fit with the inner surface.

2. The connector of claim 1 wherein the cannula does not extend beyond the collar.

3. The connector of claim 1 further including a shoulder formed on an open end of the collar for engaging a cooperating surface of the needleless injection site for limiting movement of the cannula into engagement with the diaphragm.

4. The connector of claim 1 wherein the enlarged annular land portion includes a forward surface between the outer surface and the cannula, the forward surface extending into engagement with the exposed surface of the thin diaphragm.

5. The connector of claim 1 wherein the thin diaphragm includes a slit defined by opposing slit edges where, in an open position of the thin diaphragm, the cannula applies a pressing force on the thin diaphragm sufficient to separate the opposing slit edges a distance less than an outer diameter of the cannula.

6. The connector of claim 1 including an end of the connector, opposite from the cannula, defining a passage for engaging a luer taper.

* * * * *